United States Patent
Grage, Jr. et al.

(10) Patent No.: US 11,998,573 B2
(45) Date of Patent: Jun. 4, 2024

(54) COMPOSITION AND METHOD FOR TREATMENT OF DRY EYE SYNDROME

(71) Applicant: Oculiant LLC, Johns Creek, GA (US)

(72) Inventors: Henry M. Grage, Jr., Johns Creek, GA (US); Ajit Nemi, Atlanta, GA (US)

(73) Assignee: Oculiant, LLC, Johns Creek, GA (US)

( * ) Notice: Subject to any disclaimer, the term of this patent is extended or adjusted under 35 U.S.C. 154(b) by 0 days.

(21) Appl. No.: 17/748,028

(22) Filed: May 19, 2022

(65) Prior Publication Data

US 2022/0370512 A1    Nov. 24, 2022

Related U.S. Application Data

(60) Provisional application No. 63/190,764, filed on May 19, 2021.

(51) Int. Cl.

| | | |
|---|---|---|
| A61K 35/644 | (2015.01) | |
| A61K 9/00 | (2006.01) | |
| A61K 33/22 | (2006.01) | |
| A61K 47/02 | (2006.01) | |
| A61K 47/08 | (2006.01) | |
| A61K 47/10 | (2017.01) | |
| A61K 47/36 | (2006.01) | |
| A61K 47/38 | (2006.01) | |
| A61P 27/04 | (2006.01) | |

(52) U.S. Cl.
CPC .......... *A61K 35/644* (2013.01); *A61K 9/0048* (2013.01); *A61K 33/22* (2013.01); *A61K 47/02* (2013.01); *A61K 47/08* (2013.01); *A61K 47/10* (2013.01); *A61K 47/36* (2013.01); *A61K 47/38* (2013.01); *A61P 27/04* (2018.01)

(58) Field of Classification Search
None
See application file for complete search history.

(56) References Cited

U.S. PATENT DOCUMENTS

2010/0233283 A1* 9/2010 Moloney .............. A61K 35/644
424/537

* cited by examiner

*Primary Examiner* — Russell G Fiebig
(74) *Attorney, Agent, or Firm* — Denton Intellectual Property Law Firm, LLC; F. Russell Denton, Esq.

(57) ABSTRACT

The invention provides compositions and methods of treatment for Dry Eye Syndrome wherein they do not irritate an eye of a human patient who is in need thereof. In particular the invention provides methylglyoxal and Manuka honey in ratios and grades that relieve symptoms and causes of DES without causing irritation to the affected eye(s).

20 Claims, No Drawings

COMPOSITION AND METHOD FOR TREATMENT OF DRY EYE SYNDROME

RELATED APPLICATIONS

This application claims priority from U.S. provisional application 63/190,764 having the same title and coinventors, filed May 19, 2021.

FIELD OF INVENTION

This invention concerns compositions for treatment of Dry Eye Syndrome, and methods of treatment of Dry Eye Syndrome using those compositions.

FEDERAL FUNDING

The inventors used no federal funds for discovery or development of this invention.

BACKGROUND

Dry Eye Syndrome (DES) is one of several names for a common medical condition. Some others are keratoconjunctivitis sicca (KCS), keratitis sicca, and dry eye disease. Typical complaints include a pulling sensation, pressure behind the eye, a feeling of a speck of dirt in the eye, and sensitivity to bright light. Other symptoms may include redness, burning, discharge, blurred vision, gritty irritation, and easily fatigued eyes.

DES produces dryness in two eye parts: the conjunctiva membrane that lines the inner eyelids and covers the white of the eye; and the cornea, a clear layer in front of the iris and pupil. The syndrome arises from either insufficient tears or their too-rapid evaporation. Ironically this can lead to eye watering (emergency tearing), yet those tears do not lubricate the eyes so they cannot relieve symptoms. Several factors trigger the appearance of DES, including age 40 or more, adenoviruses, contact lens use, gland dysfunction, diabetes, pregnancy, Sjögren syndrome, vitamin A deficiency, LASIK and other eye surgeries, dry air (such as an arid climate, airplane cabin, or hair drying zone), or use of drugs such as antihistamines, blood pressure medications, hormone replacement therapy, or antidepressants. Chronic exposure to dust, tobacco smoke or infection can also lead to DES.

DES occurs regardless of race. The incidence of DES ranges from 5% to 50% around the globe, and up to 70% among the elderly. For U.S. adults the National Health and Wellness Survey found an incidence of 6.8%. But up to 20% of U.S. adults have experienced DES, and it afflicts up to 4 million U.S. adults in the age range 65-84. Usually but not always DES patients suffer in both eyes. In some patients the symptoms are mild and occasional; but in other cases DES is severe and continuous. Most patients have no long-term eye damage, but untreated DES can lead to impairment or even loss of vision.

At present there is no known permanent cure for DES. Most treatments fall into one of five categories: (1) avoidance of causes; (2) stimulating or supplementing tears; (3) increasing tear retention; (4) eyelid hygiene; and (5) treating inflammation of the eyes. These are explained below.

The first category, risk avoidance, includes limiting exposure to smoke, dust, infections, dry air, drafts, and blasts of hot air. And for instance, indoor humidifiers may be used. The effectiveness of this approach depends on hazards at home and at work, and on the patient's ability to self-quarantine.

As to tear supplementation, the most popular remedy is administration of artificial tears every few hours throughout the day. Patients may also be taught to blink more often, such as when looking at computer screens. Some patients benefit from applying a thicker lubricating gel or ointment to the inside of the lower eyelid. These lubricants commonly contain petroleum jelly, mineral oil, or similar ingredients. These gels and ointments coat the eye and inside of the eyelid like a layer of oil on water, so they have the added benefit of limiting evaporation of natural tears. Ointments blur the vision and are not compatible with contact lenses, so usually they are used primarily at bedtime. It is not known which formulation paradigms work best. In patients with moderate to severe dry eye syndrome, autologous serum tears have demonstrated enhanced therapeutic effect compared to traditional artificial tears in some individuals. However, this can be an expensive treatment that requires patients to have their blood drawn at regular intervals.

Thirdly, tear retention is improved by collagen and silicone lacrimal plugs that prevent drainage of tears from the ocular surface. Close-fitting wrap-around glasses are sometimes used at bedtime to limit evaporation by creating a moisture chamber. The plugs are reserved for patients with moderate to severe cases of DES because of the risk of tearing, infection, and swelling of tear ducts.

Eyelid hygiene is a critical component of treatment in patients suffering from evaporative dry eye. These individuals suffer from meibomian gland dysfunction, whereby the oil glands on the eyelids near the eyelashes produce thicker secretions compared to the normal "olive oil"-like fluid that is released from these glands. As this secretion comprises the outer layer of the normal tear film, individuals suffering from dry eye syndrome often have an unstable tear film that evaporates m readily. Eyelid hygiene consists of first applying warm compresses for ten minutes once or twice daily to help liquefy the secretions and to loosen up crusting along the eyelid margins. The second part involves eyelid scrubs with baby shampoo or commercial eyelid cleansers which keeps the eyelid margins clean and gland openings unobstructed. However, compliance is often an issue: for patients who need to perform this regimen on a daily basis.

In recent years, there has been a paradigm shift in management of dry eye syndrome as researchers and clinicians now understand it to be a progressive, inflammatory condition. Topical steroid eye drops have been used for years to help manage DES symptoms as steroids decrease inflammation. However, they may only be used for short intervals of time due to risk of elevated intraocular pressure (glaucoma) and cataract formation. Topical cyclosporine has been an advancement in treatment of dry eyes as it is an immune-modulating medication that may safely be used long-term without the side effects of steroids. More recently, another medicine named lifitegrast has been approved; it addresses a different part of the inflammatory cascade. While these are helpful therapeutic remedies for patients who have moderate to severe dry eyes, these treatments have side effects of stinging, burning, bitter taste, and transient blurred vision. In addition, these medications are expensive and cost-prohibitive for many individuals.

More invasive countermeasures have also been explored, such as: cauterizing eye puncta (small drainage openings for tears) to seal them with scar tissue; heating the eye's oil glands to unclog them; and partially sewing the eyelids together to reduce tear evaporation. Each of these introduces new medical risks.

Dogs, cats, and horses may also suffer from DES. Indeed, a dozen canine breeds are particularly vulnerable to it, including the: cavalier King Charles spaniel; English bulldog; lhasa apso; shih tzu; west highland white terrier; pug; bloodhound; American cocker spaniel; pekingese; Boston terrier; miniature schnauzer and samoyed. Most cases have a genetic basis, but chronic conjunctivitis, distemper, and drugs such as sulfasalazine and trimethoprim-sulfonamide also cause them. In cats the main cause is chronic conjunctivitis, especially with feline herpesvirus.

Veterinary treatments employ tear replacers containing thickeners such as methylcellulose or carboxymethyl cellulose, together with cyclosporine. Less commonly, topical antibiotics and corticosteroids are administered. In extreme cases parotid duct transposition surgery is conducted, in order to replace tears with saliva.

In light of the ongoing challenges presented by DES, and in particular in view of the expense and patient discomfort associated with remedies in the prior art, there is an ongoing need for improved methods to treat Dry Eye Syndrome.

SUMMARY OF THE INVENTION

The invention provides compositions and methods of treatment for Dry Eye Syndrome wherein they do not irritate an eye of a human patient who is in need thereof. In particular the invention provides methylglyoxal and Manuka honey in ratios and grades that relieve symptoms and causes of DES without causing irritation to the affected eye(s).

In a particular embodiment the invention is a composition that is suitable for treatment of Dry Eye Syndrome (DES), wherein the composition is aqueous and comprises:
  a) boric acid in a concentration ranging from 0.5 to 2.0 mg/mL;
  b) a boric acid salt in a concentration ranging from 0.0 to 0.5 mg/mL by dry weight as added to the composition;
  c) one or more metal chloride salts in a total concentration ranging from 3.0 to 10.0 mg/mL;
  d) a water-soluble hyaluronate polymer in a concentration ranging from 0.5 to 2.5 mg/mL;
  e) a water-soluble cellulose polymer in a concentration ranging from 2.5 to 7.5 mg/mL;
  f) a polyhydric alcohol selected from the group consisting of natural monosaccharides, sugar alcohols, amino sugars, and dihydroxy propanes, wherein the polyhydric alcohol is present in a concentration ranging from 2.0 to 20.0 mg/mL glycerin;
  g) a chlorite or hypochlorite salt, in a concentration ranging from 0.01 to 0.10 mg/mL;
  h) added methylglyoxal in a concentration ranging from 0.01 to 0.10 mg/mL; and
  i) manuka honey in a concentration ranging from 0.5 to 1.5 mg/mL;
  wherein the respective concentrations of methylglyoxal and manuka honey are in a ratio that is in the range of 1:10 to 1:50, and
  wherein the concentration of each of methylglyoxal and manuka honey is at a level that is not irritating when administered to an eye of a human patient who suffers from DES.

In another embodiment the invention is a method of therapeutic treatment for dry eye syndrome (DES) comprising administering to a patient in need thereof a pharmaceutically efficacious amount of an aqueous composition comprising:
  a) boric acid in a concentration ranging from 0.5 to 2.0 mg/mL;
  b) a boric acid salt in a concentration ranging from 0.0 to 0.5 mg/mL;
  c) one or more metal chloride salts in a total concentration ranging from 3.0 to 10.0 mg/mL;
  d) a water-soluble hyaluronate polymer in a concentration ranging from 0.5 to 2.5 mg/mL;
  e) a water-soluble cellulose polymer in a concentration ranging from 2.5 to 7.5 mg/mL;
  f) a polyhydric alcohol selected from the group consisting of natural monosaccharides, sugar alcohols, amino sugars, and dihydroxy propanes, wherein the polyhydric alcohol is present in a concentration ranging from 2.0 to 20.0 mg/mL glycerin;
  g) a chlorite or hypochlorite salt, in a concentration ranging from 0.01 to 0.10 mg/mL;
  h) added methylglyoxal in a concentration ranging from 0.01 to 0.10 mg/mL; and
  i) manuka honey in a concentration ranging from 0.5 to 1.5 mg/mL;
  wherein the methylglyoxal and manuka honey are in a ratio of respective concentrations that is in a range from 1:10 to 1:50, and
  wherein each of methylglyoxal and manuka honey is at a concentration that is not irritating when administered to an eye of a human patient who suffers from DES.

DETAILED DESCRIPTION OF THE INVENTION

Definitions

The invention may be better understood by consideration of the following definitions for terms as used herein.

The term "composition" has its usual and ordinary meaning in the chemical arts, and includes both homogeneous and heterogeneous liquid mixtures, but is not so limited. In some embodiments the composition is a liquid mixture containing solid particles that are at least 1 nanometer wide at their greatest diameter, wherein the particles are undissolved ingredients in the mixture.

The terms "Dry Eye Syndrome" and DES refer to a common medical condition known by those names and or as keratoconjunctivitis sicca (KCS), keratitis sicca, or dry eye disease. Non-limiting illustrative symptoms of DES include: a pulling sensation at an eye; pressure behind an eye; a feeling of a speck of dirt in an eye; sensitivity to bright light; redness of an eye; a burning sensation in an eye; ocular discharge; blurred vision; gritty irritation of an eye; and an easily fatigued eye. Non-limiting illustrative factors that can trigger DES include: patient age 40 or more; infection with an adenovirus; contact lens use; gland dysfunction; diabetes; pregnancy; Sjögren syndrome; vitamin A deficiency; a LASIK operation; another type of eye surgery; dry air in an arid climate; dry air in an airplane cabin; dry air in a hair drying zone; antihistamine use; use of a blood pressure medication; use of a hormone replacement therapy; use of an antidepressant; chronic exposure to dust; chronic exposure to tobacco smoke; and a chronic infection. The terms as used here for these symptoms and illustrative factors have the same respective meanings that would be ascribed to them by a physician of ordinary skill in the medical arts of eye care. The term "trigger" as used herein with respect to symptoms triggered by factors means that the symptom is commonly manifested in the presence of such factors, whether the factor causes the symptom directly or not.

The term "symptom" as used herein has its usual and ordinary meaning in the medical arts.

The term "treatment" as used for treatment of a medical condition contemplates therapeutic treatment to mitigate symptoms and or resolve a cause of that condition. In some embodiments the term contemplates preventative treatment but the term is no so limited.

The term "suitable for treatment" as used with respect to a composition for treating DES means that the composition is: (1) capable of being administered topically on the eye as drops of a fluid, as the term fluid is understood in the medical arts; and (2) is capable of alleviating discomfort associated with DES.

The term "therapeutic" as used with respect to treatment means that it is intended to treat an existing condition.

The term "method of therapeutic treatment" as used with respect to compositions of the invention to treat Dry Eye Syndrome concerns topical application of one or more drops of those composition upon or near to the surface of a patient's eye.

The term "aqueous" as used with reference to a composition means that it contains a substantial proportion of water, and in particular embodiments means that the minimum amount of water that the composition contains by weight is selected from the group consisting of: 50%, 55%, 60%, 65%, 70%, 75%, 80%, 85%, 90%, and 95%.

The term "water" means $H_2O$ and has its usual and ordinary meaning in the chemical arts.

The term "boric acid" as used with respect to an ingredient in a composition means $B(OH)_3$. The term "boric acid salt" as used with respect to an ingredient in a composition includes salts such as $M^+B^-(OR')(OR'')(OR''')(OR'''')$ where $M^+$ is $H^+$, $Na^+$, $K^+$, or $(Mg^{2+})_{1/2}$ and where R', R'', R''', and R'''' are independently selected from H, a sugar moiety in a hyaluronate polymer, a sugar moiety in a cellulose polymer, a sugar moiety in manuka honey, or a polyhydric alcohol.

The term "glycerol" and "glycerin(e)" are synonymous and have their usual and ordinary meaning in the chemical arts.

The term "dry weight" means weight in the absence of all water molecules, including the absence of waters of hydration. The term "by dry weight as added to the composition" means the weight before addition to water in the composition. The term "by dry weight, relative to water in the composition" compares the dry weight added to the amount of water in the composition, independent of other ingredients in the composition.

The term "metal salt" means a salt having a metal cation, as metals are identified in the periodic table, e.g., at columns I, II, the transition metals, and the post-transition metals. The term "small molecule" metal salt means that the salt does not comprise a polymer and by dry weight the molecular weight is no more than 1,000 atomic units.

The term "metal chloride salt" means a chloride salt of sodium, potassium, magnesium, calcium, manganese, iron, copper, or zinc.

The term "water-soluble hyaluronate polymer" means a polymer of a salt of hyaluronic acid that can be dissolved essentially completely in water. Non-limiting examples include the sodium salt (CAS No. 9067-32-7) and potassium salt (CAS No. 31799-9104) but the invention is not so limited. Hyaluronic acid has its usual meaning in organic chemistry and biochemistry, for the compound with CAS No. 9004-61-9 and IUPAC name poly{[(2S,3R,4R,5S,6R)-3-acetamido-5-hydroxy-6-(hydroxymethyl)oxane-2,4-diyl]oxy[(2R,3R,4R,5S,6S)-6-carboxy-3,4-dihydroxyoxane-2,5-diyl]oxy}, and includes derivatives, oligomers, oligomeric hydrolysates, and polydisperse compositions thereof, provided that they dissolve essentially completely in water. By derivative is meant derivatives such as acetyl derivatives, methyl derivatives, ethyl derivatives, hydroxypropylmethyl derivatives, and hyaluronic acid bonded to moieties such as are added to cellulose in water-soluble cellulose varieties.

The term "water-soluble cellulose polymer" means cellulose that has been bonded to a moiety such as methyl, ethyl, hydroxypropylmethyl, or other moiety wherein the thusly bonded cellulose is capable of dissolving essentially completely in water. By "essentially completely" is meant that ≤0.1 weight percent of the cellulose polymer remains undissolved.

The term "polyhydric alcohol" means a chemical species that has a plurality of alcohol groups. In particular it includes dihydroxy ethane, 1,2- and 1,3-dihydroxy propane, glycerin, pentaerythritol, five- and six-carbon natural sugars, sugar alcohols, monosaccharides, disaccharides, oligosaccharides, polysaccharides, and amino sugars; as used herein these terms have their usual meanings in the chemical arts.

The term "chlorite salt" means a salt the includes the anionic species $ClO_2^-$. The term "salt" has its usual and ordinary meaning in the chemical arts.

The term "hypochlorite salt" means a salt the includes the anionic species $ClO^-$.

The terms "methylglyoxal" and "MGO" are synonymous and mean the compound having structure $H_3C-C(=O)-C(=O)-H$. Non-limiting illustrative concentrations of methylglyoxal and manuka honey in compositions according to the invention are in a ratio selected from a range of: 1:12 to 1:40; 1:14 to 1:30; 1:15 to 1:20; or 1:17.5.

The term "manuka honey" means the substance known by that name for any officially recognized grade in Australia or New Zealand. In particular it includes any of the following official national grades: New Zealand monofloral grade; New Zealand multifloral grade; Austrialan authentic grade; and Australian authorized grade.

The term "concentration" has its usual and ordinary meaning in chemistry for a substance dissolved in a liquid. The term "at a level", when it refers to a concentration, means the magnitude of concentration. The term "respective" as used herein with reference to concentrations means, when those concentrations are considered specifically to the compositions on which they are based. As used herein ranges of concentrations are inclusive of the end values, e.g., "0.5 to 2.0 mg/ml" means 0.5 mg/mL≤concentration ≤2.0 mg/mL.

The term "ratio" has its usual and ordinary mathematical meaning of relative proportions. Where it is used herein to compare concentrations, the proportions should be compared. E.g., for concentrations of 0.05 mg/ml added methylglyoxal (MGO) and 1.0 mg/mL manuka honey (MH), the MGO:MH ration would be 0.05:1.0=1:20.

The term "not irritating" as used with respect to a concentration of a substance administered to the eye of a human patient means that the patient does not deem the substance or its concentration to be irritating to the eye on a subjective medical scale of ocular discomfort. An illustrative example of a subjective medical scale of ocular discomfort is provided in the tables shown at Examples 1 and 2 herein, but the invention is not so limited. The term "subjective eye discomfort score" and like terms refer to a patient's designation of his or her relative degree of discomfort or pain to the eye, by means of such a survey, form or scale. When such a score is reduced, that effect is referred to herein as lowering, decreasing, reducing, diminishing, or like terms, relative to an initial subjective score before the lowering was effected.

The term "patient" means a person in need of medical care. The term "human" has its usual and ordinary meaning in the medical arts, specifically *Homo sapiens*. The term "suffers from DES" as used to describe a patient means that person has at least one symptom associated with DES, which may include but are not limited to those listed in the definition of Dry Eye Syndrome herein.

The term "applying" as used with respect to one or more drops applied to an eye for medical treatment means topical application of the drop(s) upon or near to the surface of an eye. Reference to the number of drops applied per day means the number applied within a 24-hour period. Reference to a treatment period for such applications refers to the length of time over which drops are administered. For example the treatment period may be at least 2 days, at least 3 days, at least 5 days, at least 1 week, at least 10 days, at least 2 weeks, at least 20 days, or at least a higher number of days but the invention is not so limited. In further embodiments the treatment period is capped at a threshold duration such as under one of: 5 days, 10 days, 15 days, 20 days, 25 days, 30 days, 60 days, 90 days, 6 months, or 1 year; but the invention is not so limited.

The term "official national grade" as used with respect to manuka honey from New Zealand and or Australia carries the respective meanings ascribed to it by law in those respective nations. The terms "New Zealand monofloral grade", "New Zealand multifloral grade", "Austrialan authentic grade", and "Australian authorized grade" likewise refer to compositions defined by legal standards in those respective nations.

The term "additive" as used with respect to an aqueous composition means a substance that serves as the additive and is dissolved in the composition. The term "polymeric additive" means an additive that is a polymer by nature, such as but not limited to hyaluronic acid, its derivatives, cellulose, and derivatives of cellulose.

The terms "administer" and "administration" as used with respect to a drug for DES means that it is provided topically to the eye.

The term "pharmaceutically efficacious" as used with respect to an amount of a composition means that the amount is sufficient to provide symptom relief or another medicinal benefit for treatment of DES to a patient in need thereof.

The term "significant relief" as used with respect to relief of a patient's pain from DES by administration of a composition or method according the invention means that use of that composition or method results in at least a 20 percent reduction in discomfort in a human patient within 20 days of treatment with it, when the reduction in discomfort is gauged by a subjective scoring of the discomfort.

DESCRIPTION

The present invention aims to leverage natural products to improve treatment of DES.

Manuka honey is derived from the flowering *Leptospermum* genus. The best-known species is known colloquially as manuka, broom tree, or New Zealand tea tree. The species grows as an evergreen tree or shrub; it is from the myrtle family and is native to New Zealand and Southeast Australia. The honey is made by the so-called European honeybee from any of 80 *Leptospermum* species in those areas. The product's aroma has been described as "damp earth, heather, aromatic". And its flavor has been called "earthy, oily, herbaceous", "florid, rich and complex", and "mineral, slightly bitter". If at least 50% of the honey is obtained by the bees from one (manuka-based) source, it is deemed monofloral, otherwise it is deemed multifloral.

The main uses of the medical (i.e., sterilized) form of this honey are for wounds and burns. Manuka honey's antimicrobial active ingredient differs from other honeys in that it is methylglyoxal (MGO) instead of hydrogen peroxide. The chemical structure of MGO is $CH_3C(O)CHO$. The glucose oxidase enzyme is responsible for peroxide accumulation in other honeys, but MGO suppresses that enzyme. Also, unlike for antibiotics, bacteria are not known to become resistant to MGO.

For a monofloral label claim, manuka honey from New Zealand must be produced in that nation and meet a five-fold quality standard of: (a) 400 mg/kg 3-phenyllactic acid; (b)≥5 mg/kg 2'-methoxyacetophenone; (c)≥1 mg/kg 2-methoxybenzoic acid; (d)≥1 mg/kg 4-hydroxyphenyllactic acid; and (e)≥3 fg/uL of manuka pollen DNA as determined by one DNA marker. For a multifloral label claim, it is sufficient to have 20-399 mg/kg 3-phenyllactic acid and ≥1 mg/kg 2'-methoxyacetophenone, with the other three criteria remaining the same.

The Australian standard for manuka honey requires that it is produced in that nation and meet minimum thresholds for methylglyoxal (MGO) and dihydroxyacetone (DHA). The "authentic" grade has >85 mg/kg (or ppm) MGO and >170 mg/kg DHA. The "authorized" grade has >30 mg/kg (or ppm) MGO and >60 mg/kg DHA. Leptosperin is also sometimes used as a distinctive marker for manuka honey; the compound is present there at 100-1,000 mg/kg, and is a small molecule: methyl syringate β-D-gentiobioside.

Past attempts by others have found that substantial concentrations of manuka honey could show a benefit against Dry Eye Syndrome after 8 weeks of use, but caused burning symptoms to the eye when applied. There a minimum of 16% manuka honey was applied together with warm compresses, lid massage and preservative-free lubricant, in participants with evaporative dry eye due to moderate to advanced meibomian gland dysfunction. See, J. M., Albietz and K. L. Schmid, "Randomised controlled trial of topical antibacterial Manuka (*Leptospermum* species) honey for evaporative dry eye due to meibomian gland dysfunction," Clin. Exp. Optom., 100(6):603-615 (November 2017), Epub 2017 Jun. 6.

This observation of burning effects at the effective concentrations weighs against use for DES. And for other reasons researchers have advocated against MGO because of its role in diabetic adverse effects. N. Rabbani and P. J. Thornalley, "The critical role of methylglyoxal and glyoxalase I in diabetic nephropathy".

We have now surprisingly discovered that manuka dosing that would be grossly inferior in view of prior literature can provide superior benefits for DES without irritating the eyes.

The present inventors conducted a number of trials both on themselves and on Dr. Nemi's patients to determine the concentration that resulted in no burning sensation upon application. Dilutions of manuka honey were then prepared that were respectively 10%, 20%, 40% and 80% lower than those found in nature. Then MGO solutions were formulated that were respectively 10%, 20%, 40% and 80% greater than those found naturally in Manuka honey. These honey dilutions and MGO solutions were formulated as prototype eyedrops and again tested on the present inventors and on coinventor Dr. Nemi's patients to find the threshold below which there is no burning sensation. Further work led to the formulation below, in distilled water.

| Final Concentration | Ingredient | Equivalent Concentration |
|---|---|---|
| 1.20 mg/mL | Boric Acid | |
| 0.20 mg/mL | Sodium Borate | |
| 2.52 mg/mL | Sodium Chloride | |
| 2.52 mg/mL | Magnesium Chloride | |
| 2.52 mg/mL | Potassium Chloride | |
| 1.50 mg/mL | Sodium Hyaluronate | |
| 5.00 mg/mL | Sodium Carboxymethylcellulose | |
| 1.00 % | Glycerin | 10.000 mg/mL |
| 0.004 % | Sodium Chlorite | 0.040 mg/mL |
| 0.0035 % | Methylglyoxal | 0.035 mg/mL |
| 0.10 % | Manuka Honey | 1.000 mg/mL |
| | TOTAL ADDITIVES | 26.535 mg/mL |
| | TOTAL WATER | 973.465 mg/mL |

This contrasts with the 16% to 25% concentrations of manuka honey sold for topical application. The present invention's reduction of manuka honey dropped its concentration by 200-fold and reduced the honey-component MGO in the formulation to the same degree. Adding back pure MGO to just below the point of irritation shifted the total from 0.04% MGO before honey dilution to 0.0035% MGO after dilution and restoration. That represented a 11.5-fold reduction in MGO for the non-irritating eyedrop composition of the invention. This corresponds to a 17.4:1 ratio of the invention's MGO concentration versus manuka honey MGO concentration.

Results:

Volunteer Trial: Patients with severe discomfort due to DES were asked to apply 1 or 2 drops per day to each affected eye for 10 to 20 days. We prepared a questionnaire to quantitate the effect (see Examples 1 and 2) and asked each patient to independently complete the form and send it back to us. Of 20 patients in this trial, 19 returned the questionnaire. The scoring was for a range from 0 points (no discomfort ever) to 24 points (always feeling discomfort for all 6 parameters). The cumulative findings are below: average pain scores were at least halved.

| N = 19 | Pre-Treatment | Post-Treatment |
|---|---|---|
| Mean | 14.39 | 6.11 |
| Std. Dev. | 4.12 | 3.42 |

EXAMPLE 1: Dry Eye Treatment Questionnaire Before Eye Drops

The following survey was used before treatment, and served as the baseline for determining reduction in each patient's scoring of subjective eye discomfort.

| Please check the appropriate box for each question. Do your eyes ever feel dry? Do you ever feel a gritty or sandy sensation in your eyes? Do you ever experience a burning sensation in your eyes? Do you ever experience tearing in your eyes? Do you ever experience redness in your eyes? Do you ever experience itching in your eyes? | Never (Score 0) | Rarely (Score 1) | Sometimes (Score 2) | Often (Score 3) | Always (Score 4) |
|---|---|---|---|---|---|

EXAMPLE 2: Dry Eye Treatment Questionnaire After Eye Drops

The following survey was used after treatment, and served as the end point for determining reduction in each patient's scoring of subjective eye discomfort.

| Please check the appropriate box for each question. Do your eyes ever feel dry? Do you ever feel a gritty or sandy sensation in your eyes? | Never (Score 0) | Rarely (Score 1) | Sometimes (Score 2) | Often (Score 3) | Always (Score 4) |
|---|---|---|---|---|---|

-continued

Do you ever experience a burning sensation in your eyes?
Do you ever experience tearing in your eyes?
Do you ever experience redness in your eyes?
Do you ever experience itching in your eyes?

The embodiments of the invention as described herein are merely illustrative and are not exclusive. Numerous additions, variations, derivations, permutations, equivalents, combinations and modifications of the above-described invention will be apparent to persons of ordinary skill in the relevant arts and are within the scope and spirit of the invention. The invention as described herein contemplates the use of those alternative embodiments without limitation.

The invention claimed is:

1. A composition for treatment of Dry Eye Syndrome (DES), wherein the composition is aqueous and comprises:
   a) boric acid in a concentration ranging from 0.5 to 2.0 mg/mL;
   b) a boric acid salt in a concentration ranging from 0.0 to 0.5 mg/mL by dry weight as added to the composition;
   c) one or more metal chloride salts in a total concentration ranging from 3.0 to 10.0 mg/mL;
   d) a water-soluble hyaluronate polymer in a concentration ranging from 0.5 to 2.5 mg/mL;
   e) a water-soluble cellulose polymer in a concentration ranging from 2.5 to 7.5 mg/mL;
   f) a polyhydric alcohol selected from the group consisting of natural monosaccharides, sugar alcohols, amino sugars, and dihydroxypropanes, wherein the polyhydric alcohol is present in a concentration ranging from 2.0 to 20.0 mg/mL glycerin;
   g) a chlorite or hypochlorite salt, in a concentration ranging from 0.01 to 0.10 mg/mL;
   h) a pharmaceutically effective amount of added methylglyoxal (MGO) in a concentration ranging from 0.01 to 0.10 mg/mL; and
   i) a pharmaceutically effective amount of manuka honey in a concentration ranging from 0.5 to 1.5 mg/mL;
   wherein the methylglyoxal and manuka honey are in a ratio of respective concentrations that is in a range of 1:10 to 1:50, and
   wherein each of methylglyoxal and manuka honey is at a concentration that is not irritating when administered to an eye of a human patient who suffers from DES.

2. The composition of claim 1 wherein the respective concentrations of methylglyoxal and manuka honey are in a ratio that is selected from the range of: 1:12 to 1:40; 1:14 to 1:30; 1:15 to 1:20; or about 1:17.5.

3. The composition of claim 1 wherein the manuka honey is selected from at least one of the following official national grades: New Zealand monofloral grade; New Zealand multifloral grade; Australian authentic grade; and Australian authorized grade.

4. The composition of claim 1 wherein the composition comprises 0.0035%+0.0015% MGO.

5. The composition of claim 1, comprising at least 95% water by weight.

6. The composition of claim 1, comprising no more than 3.0% additives by dry weight, relative to water in the composition.

7. The composition of claim 1, comprising no more than 1.0% polymeric additives by dry weight.

8. The composition of claim 1, comprising no more than 1.0% added small-molecule metal salts by dry weight.

9. The composition of claim 1, comprising no more than 0.5% boric acid by dry weight.

10. The composition of claim 1, comprising no more than 1.0% glycerol by dry weight.

11. A method of therapeutic treatment for dry eye syndrome (DES) comprising administering to a patient in need thereof a pharmaceutically efficacious amount of an aqueous composition comprising:
   a) boric acid in a concentration ranging from 0.5 to 2.0 mg/mL;
   b) a boric acid salt in a concentration ranging from 0.0 to 0.5 mg/mL;
   c) one or more metal chloride salts in a total concentration ranging from 3.0 to 10.0 mg/mL;
   d) a water-soluble hyaluronate polymer in a concentration ranging from 0.5 to 2.5 mg/mL;
   e) a water-soluble cellulose polymer in a concentration ranging from 2.5 to 7.5 mg/mL;
   f) a polyhydric alcohol selected from the group consisting of natural monosaccharides, sugar alcohols, amino sugars, and dihydroxypropanes, wherein the polyhydric alcohol is present in a concentration ranging from 2.0 to 20.0 mg/mL glycerin;
   g) a chlorite or hypochlorite salt, in a concentration ranging from 0.01 to 0.10 mg/mL;
   h) a pharmaceutically effective amount of added methylglyoxal (MGO) in a concentration ranging from 0.01 to 0.10 mg/mL; and
   i) a pharmaceutically effective amount of manuka honey in a concentration ranging from 0.5 to 1.5 mg/mL;
   wherein the methylglyoxal and manuka honey are in a ratio of respective concentrations that is in a range from 1:10 to 1:50, and
   wherein each of methylglyoxal and manuka honey is at a concentration that is not irritating when administered to an eye of a human patient who suffers from DES.

12. The method according to claim 11 wherein the composition is administered by applying 1 or 2 drops per day to each affected eye for a treatment period selected from at least 10 days and at least 20 days.

13. The method according to claim 11 wherein the treatment provides significant relief when 1 or 2 drops per day are administered to each affected eye for a treatment period selected from at least 10 days and at least 20 days.

14. The method according to claim 11 wherein the method lowers a patient's subjective eye discomfort scores by at least 50% within 10 to 20 days.

15. The method according to claim 11 wherein the DES includes at least one symptom selected from the group consisting of: a pulling sensation at an eye; pressure behind an eye; a feeling of a speck of dirt in an eye; sensitivity to bright light; redness of an eye; a burning sensation in an eye; ocular discharge; blurred vision; gritty irritation of an eye; and an easily fatigued eye.

16. The method according to claim 11 wherein the DES has been triggered by one or more factors selected from the group of: patient age 40 or more; infection with an adenovirus; contact lens use; gland dysfunction; diabetes; pregnancy; Sjögren syndrome; vitamin A deficiency; a LASIK operation; another type of eye surgery; dry air in an arid climate; dry air in an airplane cabin; dry air in a hair drying zone; antihistamine use; use of a blood pressure medication; use of a hormone replacement therapy; use of an antidepressant; chronic exposure to dust; chronic exposure to tobacco smoke; or a chronic infection.

17. The method according to claim 11 wherein the manuka honey in the composition is selected from at least one of the following official national grades: New Zealand monofloral grade; New Zealand multifloral grade; Australian authentic grade; and Australian authorized grade.

18. The method according to claim 11 wherein the composition comprises 0.0035%+0.0015% MGO by weight.

19. The method according to claim 11 wherein the respective concentrations of methylglyoxal and manuka honey are in a ratio that is selected from a range of: 1:12 to 1:40; 1:14 to 1:30; 1:15 to 1:20; or 1:17.5.

20. The method according to claim 11, wherein the composition comprises no more than 0.5% boric acid by weight.

* * * * *